(12) United States Patent
Hansen et al.

(10) Patent No.: US 10,898,292 B2
(45) Date of Patent: Jan. 26, 2021

(54) SYSTEMS AND METHODS FOR LOCATING IMPLANTED WIRELESS POWER TRANSMISSION DEVICES

(71) Applicant: TC1 LLC, St. Paul, MN (US)

(72) Inventors: John Freddy Hansen, Pleasanton, CA (US); Christopher Eskildsen, Pleasant Hill, CA (US)

(73) Assignee: TC1 LLC, St. Paul, MN (US)

( * ) Notice: Subject to any disclaimer, the term of this patent is extended or adjusted under 35 U.S.C. 154(b) by 522 days.

(21) Appl. No.: 15/709,743

(22) Filed: Sep. 20, 2017

(65) Prior Publication Data

US 2018/0078329 A1    Mar. 22, 2018

Related U.S. Application Data

(60) Provisional application No. 62/397,676, filed on Sep. 21, 2016.

(51) Int. Cl.
*A61B 5/06* (2006.01)
*A61B 90/00* (2016.01)
(Continued)

(52) U.S. Cl.
CPC .............. *A61B 90/39* (2016.02); *A61B 5/062* (2013.01); *A61N 1/37229* (2013.01); *A61N 1/37247* (2013.01); *G01R 33/0206* (2013.01); *G01R 35/005* (2013.01); *G01V 3/08* (2013.01); *G01V 3/12* (2013.01); *H02J 7/025* (2013.01); *H02J 50/10* (2016.02); *H02J 50/90* (2016.02); *A61B 5/742* (2013.01); *A61B 2034/2051* (2016.02);
(Continued)

(58) Field of Classification Search
CPC ........... A61B 1/041; A61B 5/06; A61B 5/061; A61B 5/062; A61B 2560/0456
USPC ....................................................... 128/899
See application file for complete search history.

(56) References Cited

U.S. PATENT DOCUMENTS 4,041,955 A    8/1977 Kelly et al.
4,352,960 A    10/1982 Dormer et al.
(Continued)

FOREIGN PATENT DOCUMENTS

DE    202012000166 U1    6/2013
DE    102012201073 A1    7/2013
(Continued)

OTHER PUBLICATIONS

International Search Report and Written Opinion for International Patent Application No. PCT/US2017/052406, dated Nov. 30, 2017, 15 pages.
(Continued)

*Primary Examiner* — Samuel G Gilbert
(74) *Attorney, Agent, or Firm* — Armstrong Teasdale LLP

(57) ABSTRACT

A system for locating an implanted device including magnetic coils within a subject is provided. The system includes a magnetic sensor array including a plurality of magnetic sensors, the magnetic sensor array configured to measure a magnetic field generated by the implanted device, and a position detection module communicatively coupled to the magnetic sensor array, the position detection module configured to receive the measured magnetic field from the magnetic sensor array, and calculate a position of the implanted device based on the measured magnetic field.

15 Claims, 8 Drawing Sheets

(51) Int. Cl.
  *H02J 7/02* (2016.01)
  *G01V 3/08* (2006.01)
  *H02J 50/90* (2016.01)
  *H02J 50/10* (2016.01)
  *A61N 1/372* (2006.01)
  *G01R 33/02* (2006.01)
  *G01R 35/00* (2006.01)
  *G01V 3/12* (2006.01)
  *A61B 5/00* (2006.01)
  *A61B 34/00* (2016.01)
  *A61B 34/20* (2016.01)

(52) U.S. Cl.
  CPC . *A61B 2034/254* (2016.02); *A61B 2090/3954* (2016.02)

(56) References Cited

U.S. PATENT DOCUMENTS

| | | | |
|---|---|---|---|
| 4,561,443 A | 12/1985 | Hogrefe et al. | |
| 4,561,444 A | 12/1985 | Livingston et al. | |
| 4,630,615 A | 12/1986 | Yomtov | |
| 4,679,560 A | 7/1987 | Galbraith | |
| 4,726,378 A | 2/1988 | Kaplan | |
| 4,736,747 A | 4/1988 | Drake | |
| 4,924,171 A | 5/1990 | Baba et al. | |
| 4,945,305 A | 7/1990 | Blood | |
| 5,070,223 A | 12/1991 | Colasante | |
| 5,346,458 A | 9/1994 | Affeld | |
| 5,350,413 A | 9/1994 | Miller et al. | |
| 5,425,367 A * | 6/1995 | Shapiro | A61B 5/06 128/899 |
| 5,569,156 A | 10/1996 | Mussivand | |
| 5,630,836 A | 5/1997 | Prem et al. | |
| 5,690,693 A | 11/1997 | Wang et al. | |
| 5,702,431 A | 12/1997 | Wang et al. | |
| 5,755,748 A | 5/1998 | Borza | |
| 5,771,438 A | 6/1998 | Palermo et al. | |
| 5,831,248 A | 11/1998 | Hojyo et al. | |
| 5,948,006 A | 9/1999 | Mann | |
| 6,123,726 A | 9/2000 | Mori et al. | |
| 6,149,683 A | 11/2000 | Lancisi et al. | |
| 6,212,430 B1 | 4/2001 | Kung | |
| 6,296,533 B1 | 10/2001 | Grubbs et al. | |
| 6,312,338 B1 | 11/2001 | Sato et al. | |
| 6,320,354 B1 | 11/2001 | Sengupta et al. | |
| 6,324,431 B1 | 11/2001 | Zarinetchi et al. | |
| 6,327,504 B1 | 12/2001 | Dolgin et al. | |
| 6,389,318 B1 | 5/2002 | Zarinetchi et al. | |
| 6,400,991 B1 | 6/2002 | Kung | |
| 6,442,434 B1 | 8/2002 | Zarinetchi et al. | |
| 6,451,055 B1 | 9/2002 | Weiss | |
| 6,458,164 B1 | 10/2002 | Weiss | |
| 6,478,820 B1 | 11/2002 | Weiss | |
| 6,553,263 B1 | 4/2003 | Meadows et al. | |
| 6,579,315 B1 | 6/2003 | Weiss | |
| 6,591,139 B2 | 7/2003 | Loftin et al. | |
| 6,605,032 B2 | 8/2003 | Benkowski et al. | |
| 6,647,298 B2 | 11/2003 | Abrahamson et al. | |
| 6,650,213 B1 | 11/2003 | Sakurai et al. | |
| 6,723,039 B2 | 4/2004 | French et al. | |
| 6,772,011 B2 | 8/2004 | Dolgin | |
| 6,801,807 B2 | 10/2004 | Abrahamson | |
| 6,810,289 B1 | 10/2004 | Shaquer | |
| 6,850,803 B1 | 2/2005 | Jimenez et al. | |
| 6,894,456 B2 | 5/2005 | Tsukamoto et al. | |
| 6,895,281 B1 | 5/2005 | Amundson et al. | |
| 6,949,065 B2 | 9/2005 | Sporer et al. | |
| 6,960,968 B2 | 11/2005 | Odendaal et al. | |
| 6,967,621 B1 | 11/2005 | Cadotte, Jr. et al. | |
| 6,985,773 B2 | 1/2006 | Von Arx et al. | |
| 7,015,769 B2 | 3/2006 | Schulman et al. | |
| 7,107,103 B2 | 9/2006 | Schulman et al. | |
| 7,126,310 B1 | 10/2006 | Barron | |
| 7,225,032 B2 | 5/2007 | Schmeling et al. | |
| 7,246,040 B2 | 7/2007 | Borg et al. | |
| 7,286,880 B2 | 10/2007 | Olson et al. | |
| 7,428,438 B2 | 9/2008 | Parramon et al. | |
| 7,471,986 B2 | 12/2008 | Hatlestad | |
| 7,496,733 B2 | 2/2009 | Altman et al. | |
| 7,505,816 B2 | 3/2009 | Schmeling et al. | |
| 7,515,012 B2 | 4/2009 | Schulman et al. | |
| 7,522,878 B2 | 4/2009 | Baarman | |
| 7,532,901 B1 | 5/2009 | LaFranchise et al. | |
| 7,565,187 B1 | 7/2009 | Dynok et al. | |
| 7,571,007 B2 | 8/2009 | Erickson et al. | |
| 7,574,173 B2 | 8/2009 | Terranova et al. | |
| 7,587,241 B2 | 9/2009 | Parramon et al. | |
| 7,599,743 B2 | 10/2009 | Hassler et al. | |
| 7,650,187 B2 | 1/2010 | Gruber et al. | |
| 7,650,192 B2 | 1/2010 | Wahlstrand | |
| 7,711,433 B2 | 5/2010 | Davis et al. | |
| 7,720,546 B2 | 5/2010 | Ginggen et al. | |
| 7,741,734 B2 | 6/2010 | Joannopoulos et al. | |
| 7,761,164 B2 | 7/2010 | Verhoef et al. | |
| 7,774,069 B2 | 8/2010 | Olson et al. | |
| 7,782,190 B1 | 8/2010 | Martin et al. | |
| 7,805,200 B2 | 9/2010 | Kast et al. | |
| 7,812,481 B2 | 10/2010 | Iisaka et al. | |
| 7,818,036 B2 | 10/2010 | Lair et al. | |
| 7,818,037 B2 | 10/2010 | Lair et al. | |
| 7,825,543 B2 | 11/2010 | Karalis et al. | |
| 7,830,114 B2 | 11/2010 | Reed | |
| 7,865,245 B2 | 1/2011 | Torgerson et al. | |
| 7,872,367 B2 | 1/2011 | Recksiek et al. | |
| 7,904,170 B2 | 3/2011 | Harding | |
| 7,932,696 B2 | 4/2011 | Peterson et al. | |
| 7,962,222 B2 | 6/2011 | He et al. | |
| RE42,682 E | 9/2011 | Barreras et al. | |
| 8,050,738 B2 * | 11/2011 | Minai | A61B 1/041 128/899 |
| 8,076,807 B2 | 12/2011 | Bohn et al. | |
| 8,081,925 B2 | 12/2011 | Parramon et al. | |
| 8,096,954 B2 | 1/2012 | Stahmann et al. | |
| 8,140,168 B2 | 3/2012 | Olson et al. | |
| 8,150,529 B2 | 4/2012 | Snell et al. | |
| 8,165,694 B2 | 4/2012 | Carbanaru et al. | |
| 8,185,212 B2 | 5/2012 | Carbunaru et al. | |
| 8,193,766 B2 | 6/2012 | Rondoni et al. | |
| 8,203,434 B2 | 6/2012 | Yoshida | |
| 8,244,367 B2 | 8/2012 | Wahlstrand et al. | |
| 8,247,926 B2 | 8/2012 | Issa et al. | |
| 8,258,653 B2 | 9/2012 | Kitamura et al. | |
| 8,265,770 B2 | 9/2012 | Toy et al. | |
| 8,278,784 B2 | 10/2012 | Cook et al. | |
| 8,292,052 B2 | 10/2012 | Bohori et al. | |
| 8,299,652 B2 | 10/2012 | Smith et al. | |
| 8,301,079 B2 | 10/2012 | Baarman | |
| 8,319,473 B2 | 11/2012 | Choi et al. | |
| 8,362,742 B2 | 1/2013 | Kallmyer | |
| 8,373,310 B2 | 2/2013 | Baarman et al. | |
| 8,378,522 B2 | 2/2013 | Cook et al. | |
| 8,378,523 B2 | 2/2013 | Cook et al. | |
| 8,463,395 B2 | 6/2013 | Forsell | |
| 8,489,200 B2 | 7/2013 | Zarinetchi et al. | |
| 8,551,163 B2 | 10/2013 | Aber et al. | |
| 8,562,508 B2 | 10/2013 | Dague et al. | |
| 8,581,793 B2 | 11/2013 | Carr | |
| 8,587,154 B2 | 11/2013 | Fells et al. | |
| 8,620,447 B2 | 12/2013 | D'Ambrosio et al. | |
| 8,628,460 B2 | 1/2014 | Yomtov et al. | |
| 8,629,578 B2 | 1/2014 | Kurs et al. | |
| 8,668,473 B2 | 3/2014 | Larose et al. | |
| 8,694,117 B2 | 4/2014 | Aghassian et al. | |
| 8,810,071 B2 | 8/2014 | Sauerlaender et al. | |
| 8,884,468 B2 | 11/2014 | Lemmens et al. | |
| 8,909,351 B2 | 12/2014 | Dinsmoor et al. | |
| 8,971,958 B2 | 3/2015 | Frikart et al. | |
| 8,974,373 B2 * | 3/2015 | Hasegawa | A61B 1/00016 128/899 |
| 9,002,468 B2 | 4/2015 | Shea et al. | |
| 9,106,083 B2 | 8/2015 | Partovi | |
| 9,192,704 B2 | 11/2015 | Yomtov et al. | |

(56) References Cited

U.S. PATENT DOCUMENTS

| | | | |
|---|---|---|---|
| 9,302,093 B2 | 4/2016 | Mashiach | |
| 9,515,494 B2 | 12/2016 | Kurs et al. | |
| 9,515,495 B2 | 12/2016 | Kurs et al. | |
| 9,560,787 B2 | 1/2017 | Kallmyer et al. | |
| 2002/0038138 A1 | 3/2002 | Zarinetchi et al. | |
| 2002/0087204 A1 | 7/2002 | Kung et al. | |
| 2002/0093456 A1 | 7/2002 | Sawamura et al. | |
| 2003/0171792 A1 | 9/2003 | Zarinetchi et al. | |
| 2004/0138725 A1 | 7/2004 | Forsell | |
| 2004/0256146 A1 | 12/2004 | Frericks et al. | |
| 2005/0006083 A1 | 1/2005 | Chen et al. | |
| 2005/0090883 A1 | 4/2005 | Westlund et al. | |
| 2005/0139222 A1* | 6/2005 | Minai | A61B 1/042 128/899 |
| 2005/0288743 A1 | 12/2005 | Ahn et al. | |
| 2006/0030771 A1 | 2/2006 | Levine et al. | |
| 2006/0199997 A1 | 9/2006 | Hassler et al. | |
| 2006/0271129 A1 | 11/2006 | Tai et al. | |
| 2007/0096686 A1 | 5/2007 | Jimenez et al. | |
| 2007/0123948 A1 | 5/2007 | Dal Molin | |
| 2007/0142696 A1 | 6/2007 | Crosby et al. | |
| 2007/0191706 A1 | 8/2007 | Calderon et al. | |
| 2008/0009198 A1 | 1/2008 | Marino | |
| 2008/0027293 A1 | 1/2008 | Vodermayer et al. | |
| 2008/0054638 A1 | 3/2008 | Greene et al. | |
| 2008/0100294 A1 | 5/2008 | Rohling et al. | |
| 2008/0149736 A1 | 6/2008 | Kim et al. | |
| 2008/0167531 A1 | 7/2008 | McDermott | |
| 2008/0211320 A1 | 9/2008 | Cook et al. | |
| 2009/0018616 A1 | 1/2009 | Quick et al. | |
| 2009/0051224 A1 | 2/2009 | Cook et al. | |
| 2009/0072628 A1 | 3/2009 | Cook et al. | |
| 2009/0081943 A1 | 3/2009 | Dobyns et al. | |
| 2009/0174264 A1 | 7/2009 | Onishi et al. | |
| 2009/0212736 A1 | 8/2009 | Baarman et al. | |
| 2009/0226328 A1 | 9/2009 | Morello | |
| 2009/0270679 A1 | 10/2009 | Hoeg et al. | |
| 2009/0284220 A1 | 11/2009 | Toncich et al. | |
| 2010/0019985 A1 | 1/2010 | Bashyam et al. | |
| 2010/0033021 A1 | 2/2010 | Bennett | |
| 2010/0035453 A1 | 2/2010 | Tronnes et al. | |
| 2010/0045114 A1 | 2/2010 | Sample et al. | |
| 2010/0063347 A1 | 3/2010 | Yomtov et al. | |
| 2010/0066305 A1 | 3/2010 | Takahashi et al. | |
| 2010/0069992 A1 | 3/2010 | Aghassian et al. | |
| 2010/0109958 A1 | 5/2010 | Haubrich et al. | |
| 2010/0114143 A1 | 5/2010 | Albrecht et al. | |
| 2010/0122995 A1 | 5/2010 | Thomas et al. | |
| 2010/0171368 A1 | 7/2010 | Schatz et al. | |
| 2010/0184371 A1 | 7/2010 | Cook et al. | |
| 2010/0194334 A1 | 8/2010 | Kirby et al. | |
| 2010/0210233 A1 | 8/2010 | Cook et al. | |
| 2010/0211134 A1 | 8/2010 | Forsell | |
| 2010/0222848 A1 | 9/2010 | Forsell | |
| 2010/0222849 A1 | 9/2010 | Forsell | |
| 2010/0225174 A1 | 9/2010 | Jiang | |
| 2010/0244576 A1 | 9/2010 | Hillan et al. | |
| 2010/0253340 A1 | 10/2010 | Corum et al. | |
| 2010/0256708 A1 | 10/2010 | Thornton et al. | |
| 2010/0277121 A1 | 11/2010 | Hall et al. | |
| 2010/0308939 A1 | 12/2010 | Kurs | |
| 2010/0314946 A1 | 12/2010 | Budde et al. | |
| 2010/0331919 A1 | 12/2010 | Digiore et al. | |
| 2011/0025132 A1 | 2/2011 | Sato | |
| 2011/0043050 A1 | 2/2011 | Yabe et al. | |
| 2011/0046699 A1 | 2/2011 | Mazanec et al. | |
| 2011/0101790 A1 | 5/2011 | Budgett | |
| 2011/0109263 A1 | 5/2011 | Sakoda et al. | |
| 2011/0115431 A1 | 5/2011 | Dunworth et al. | |
| 2011/0127848 A1 | 6/2011 | Ryu et al. | |
| 2011/0148215 A1 | 6/2011 | Marzetta et al. | |
| 2011/0178361 A1 | 7/2011 | Yomtov | |
| 2011/0181235 A1 | 7/2011 | Walley et al. | |
| 2011/0205083 A1 | 8/2011 | Janna et al. | |
| 2011/0234011 A1 | 9/2011 | Yi et al. | |
| 2011/0234155 A1 | 9/2011 | Chen et al. | |
| 2011/0241436 A1 | 10/2011 | Furukawa | |
| 2011/0241750 A1 | 10/2011 | Hill | |
| 2011/0245892 A1 | 10/2011 | Kast et al. | |
| 2011/0266880 A1 | 11/2011 | Kim et al. | |
| 2011/0276110 A1 | 11/2011 | Whitehurst et al. | |
| 2011/0278948 A1 | 11/2011 | Forsell | |
| 2011/0291489 A1 | 12/2011 | Tsai et al. | |
| 2011/0291613 A1 | 12/2011 | Rosik et al. | |
| 2011/0295345 A1 | 12/2011 | Wells et al. | |
| 2011/0298294 A1 | 12/2011 | Takada et al. | |
| 2011/0301667 A1 | 12/2011 | Olson et al. | |
| 2011/0313238 A1 | 12/2011 | Reichenbach et al. | |
| 2012/0001485 A1 | 1/2012 | Uchida | |
| 2012/0032522 A1 | 2/2012 | Schatz et al. | |
| 2012/0039102 A1 | 2/2012 | Shinoda | |
| 2012/0057322 A1 | 3/2012 | Waffenschmidt | |
| 2012/0065458 A1 | 3/2012 | Tol | |
| 2012/0080957 A1 | 4/2012 | Cooper et al. | |
| 2012/0091951 A1 | 4/2012 | Sohn | |
| 2012/0104997 A1 | 5/2012 | Carobolante | |
| 2012/0109256 A1 | 5/2012 | Meskins et al. | |
| 2012/0119914 A1 | 5/2012 | Uchida | |
| 2012/0146575 A1 | 6/2012 | Armstrong et al. | |
| 2012/0149229 A1 | 6/2012 | Kearsley et al. | |
| 2012/0150259 A1 | 6/2012 | Meskens | |
| 2012/0153739 A1 | 6/2012 | Cooper et al. | |
| 2012/0153954 A1 | 6/2012 | Ota et al. | |
| 2012/0157753 A1 | 6/2012 | D'Ambrosio | |
| 2012/0157754 A1 | 6/2012 | D'Ambrosio | |
| 2012/0158407 A1 | 6/2012 | Forsell | |
| 2012/0161539 A1 | 6/2012 | Kim et al. | |
| 2012/0164943 A1 | 6/2012 | Bennett | |
| 2012/0169132 A1 | 7/2012 | Choudhary et al. | |
| 2012/0169133 A1 | 7/2012 | Lisi et al. | |
| 2012/0169137 A1 | 7/2012 | Lisi et al. | |
| 2012/0169139 A1 | 7/2012 | Kudo | |
| 2012/0169278 A1 | 7/2012 | Choi et al. | |
| 2012/0175967 A1 | 7/2012 | Dibben et al. | |
| 2012/0235364 A1 | 9/2012 | Wang et al. | |
| 2012/0239118 A1 | 9/2012 | Ozawa et al. | |
| 2012/0245649 A1 | 9/2012 | Bohori et al. | |
| 2012/0245664 A1 | 9/2012 | Smith et al. | |
| 2012/0259398 A1 | 10/2012 | Chen et al. | |
| 2012/0274148 A1 | 11/2012 | Sung et al. | |
| 2012/0306433 A1 | 12/2012 | Kim et al. | |
| 2013/0007949 A1 | 1/2013 | Kurs et al. | |
| 2013/0060103 A1 | 3/2013 | Bergida et al. | |
| 2013/0119773 A1 | 5/2013 | Davis | |
| 2013/0127253 A1 | 5/2013 | Stark et al. | |
| 2013/0149960 A1 | 6/2013 | Dec et al. | |
| 2013/0159956 A1 | 6/2013 | Verghese et al. | |
| 2013/0190551 A1 | 7/2013 | Callaway et al. | |
| 2013/0197607 A1 | 8/2013 | Wilder et al. | |
| 2013/0214731 A1 | 8/2013 | Dinsmoor et al. | |
| 2013/0241306 A1 | 9/2013 | Aber et al. | |
| 2013/0241468 A1 | 9/2013 | Moshfeghi | |
| 2013/0271088 A1 | 10/2013 | Hwang et al. | |
| 2013/0289334 A1 | 10/2013 | Badstibner et al. | |
| 2013/0310630 A1 | 11/2013 | Smith et al. | |
| 2013/0320773 A1 | 12/2013 | Schatz et al. | |
| 2013/0331638 A1 | 12/2013 | Cameron et al. | |
| 2014/0005466 A1 | 1/2014 | Crosby et al. | |
| 2014/0011447 A1 | 1/2014 | Konanur et al. | |
| 2014/0028110 A1 | 1/2014 | Petersen et al. | |
| 2014/0028111 A1 | 1/2014 | Hansen et al. | |
| 2014/0031606 A1 | 1/2014 | Hansen et al. | |
| 2014/0073839 A1 | 3/2014 | Yomtov et al. | |
| 2014/0152252 A1 | 6/2014 | Wood | |
| 2014/0163644 A1 | 6/2014 | Scott et al. | |
| 2014/0265620 A1 | 9/2014 | Hoarau et al. | |
| 2014/0265621 A1 | 9/2014 | Wong et al. | |
| 2014/0275727 A1 | 9/2014 | Bonde et al. | |
| 2015/0123654 A1 | 5/2015 | Gagnon et al. | |
| 2015/0200562 A1 | 7/2015 | Kilinc et al. | |
| 2015/0207330 A1 | 7/2015 | Petersen | |
| 2015/0207331 A1 | 7/2015 | Petersen | |
| 2015/0222127 A1 | 8/2015 | Hansen et al. | |
| 2015/0222128 A1 | 8/2015 | Hansen | |

(56) References Cited

U.S. PATENT DOCUMENTS

| | | |
|---|---|---|
| 2015/0222139 A1 | 8/2015 | Petersen et al. |
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 3/1994 |
| EP | 1513241 A1 | 3/2005 |
| EP | 2130551 A1 | 9/2009 |
| EP | 2130511 A1 | 12/2009 |
| EP | 2267864 A2 | 12/2010 |
| EP | 2548612 A1 | 1/2013 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010042055 A1 | 4/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

Chargepoint, Inc.; —chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filed and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Development and Implementation of RFID Technology, Ed. Cristina Turcu, Feb. 2009, pp. 28-30, 93-97.

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"the Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

\* cited by examiner

SYSTEMS AND METHODS FOR LOCATING IMPLANTED WIRELESS POWER TRANSMISSION DEVICES

CROSS REFERENCE TO RELATED APPLICATIONS

This application claims priority to provisional application Ser. No. 62/397,676, filed Sep. 21, 2016, which is incorporated herein in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

This disclosure relates generally to methods and systems for transmitting and receiving power wirelessly, and in various respects, determining a position of an implanted coil array and providing a user interface (UI) for guiding an external coil into coupling with the implanted coil array.

BACKGROUND

Powered devices need to have a mechanism to supply power to the operative parts. Typically systems use a physical power cable to transfer energy over a distance. There has been a continuing need for systems that can transmit power efficiently over a distance without physical structures bridging the physical gap.

Systems and methods that supply power without electrical wiring are sometimes referred to as wireless energy transmission (WET). Wireless energy transmission greatly expands the types of applications for electrically powered devices. One such example is the field of implantable medical devices. Implantable medical devices typically require an internal power source able to supply adequate power for the reasonable lifetime of the device or an electrical cable that traverses the skin. Typically an internal power source (e.g., a battery) is feasible for only low power devices like sensors. Likewise, a transcutaneous power cable significantly affects quality of life (QoL), infection risk, and product life, among many drawbacks.

More recently there has been an emphasis on systems that supply power to an implanted device without using transcutaneous wiring. This is sometimes referred to as a Transcutaneous Energy Transfer System (TETS). Frequently, energy transfer is accomplished using two magnetically coupled coils set up like a transformer so power is transferred magnetically across the skin. Conventional systems are relatively sensitive to variations in position and alignment of the coils. In order to provide constant and adequate power, the two coils need to be physically close together and well aligned.

However, it can be difficult to determine a fairly accurate and precise position of the implanted coil using current imaging systems. For example, two-dimensional (2D) ultrasound is generally inadequate in reporting an accurate location of an implanted device, for various reasons. Ultrasound echolocation depends on reflection of sound waves off of materials with different densities, and a computational reconstruction of an image based on time-of-flight to the recorded echoes. Medical ultrasound equipment is calibrated for densities of materials naturally found in the human body. Higher density materials, such as those found in an implanted medical device, can sometimes generate reflections that confuse the reconstruction algorithms in the ultrasound equipment. It then falls on the experience of the operator to interpret the images. This process will at best provide an estimate of the implant depth, but not full location information (position x, y, z, and angles $\theta$, $\varphi$, $\psi$). Moreover, implant depth estimates are questionable, as they depend greatly on the pressure the operator is applying to the ultrasound probe.

Three-dimensional (3D) ultrasound uses more sophisticated reconstructive algorithms to create a 3D image of a probed volume. This may produce better results than 2D ultrasound, but large high-density objects, such as an implanted device, may still confuse the algorithms. 3D ultrasound is also not available at many locations. X-ray imaging can theoretically locate an implant in 3D space, if multiple angles are imaged, and if the implants are fitted with markers opaque to 22 keV X-rays (a common medical X-ray energy). However, this requires sophisticated X-ray imaging devices that can reconstruct a 3D image, which are not commonly available. Moreover, the absorbed dose may be too high to justify clinical uses.

In addition, current UI systems (e.g., operated by a patient) that attempt to aid in accurate and precise location of an external coil to optimize coupling with an implanted coil have proven ineffective, time-consuming, and worry-inducing. In general, alignment between an external coil and an implanted coil is adequate if the resulting coupling k exceeds some minimum threshold $k_{min}$. It is preferable if the alignment results in a coupling close to an optimum value $k_{opt}$. The optimum value $k_{opt}$ is always larger than the minimum value $k_{min}$, and smaller than or equal to a maximum coupling value $k_{max}$. During the alignment, the patient physically adjusts the position of the external coil, while watching (or listening to) feedback from a UI. However, it may be difficult to effectively present information to the patient via the UI to achieve a coupling k close to $k_{opt}$ without taking an unreasonable amount of the patient's time, or causing the patient unnecessary worry or concern.

SUMMARY OF THE DISCLOSURE

In one embodiment, a system for locating an implanted device including magnetic coils within a subject is provided. The system includes a magnetic sensor array including a plurality of magnetic sensors, the magnetic sensor array configured to measure a magnetic field generated by the implanted device, and a position detection module communicatively coupled to the magnetic sensor array, the position detection module configured to receive the measured magnetic field from the magnetic sensor array, and calculate a position of the implanted device based on the measured magnetic field.

In another embodiment, a method for locating an implanted device including magnetic coils within a subject is provided. The method includes calibrating a magnetic sensor array to create a database of sensor responses corresponding to various implant locations and orientations, positioning the magnetic sensor array proximate the subject near an expected position of the implanted device, instructing the implanted device to power the magnetic coils, measuring, using the magnetic sensor array, a magnetic field generated by the implanted device, transmitting the measured magnetic field to a position detection module, and calculating, using the position detection module, a position of the implanted device based on the measured magnetic field.

In yet another embodiment, a system for visually displaying a degree of coupling between an external coil and an implanted coil implanted within a subject is provided. The system includes the external coil, and a computing device communicatively coupled to the external coil, the computing device comprising a user interface configured to display an icon that is indicative of the degree of coupling between the external coil and the implanted coil, wherein the icon is a circle that includes a fixed outer diameter and a variable inner diameter, wherein the variable inner diameter decreases as the degree of coupling increases, and wherein the variable inner diameter increases as the degree of coupling decreases.

In yet another embodiment, a computer-implemented method for locating an implanted device including magnetic coils within a subject is provided. The computer-implemented includes calibrating, using a computing device, a magnetic sensor array to create a database of sensor responses corresponding to various implant locations and orientations, instructing, using the computing device, the implanted device to power the magnetic coils, receiving, at the computing device, a measured magnetic field acquired by the magnetic sensor array, and calculating, using the computing device, a position of the implanted device based on the measured magnetic field.

In one embodiment, the computer implemented method further includes outputting the calculated position.

In one embodiment, calibrating the magnetic sensor array includes calibrating the magnetic sensor array using a computer simulation.

In one embodiment, calibrating the magnetic sensor array includes calibrating the magnetic sensor array using measurements acquired from an actual implant.

In one embodiment, calculating a position includes calculating the position by comparing the measured magnetic field to the sensor responses in the database.

In one embodiment, calibrating a magnetic sensor array includes calibrating a magnetic sensor array including a plurality of magnetic sensors mounted to a rigid platform.

In one embodiment, calibrating a magnetic sensor array includes calibrating a magnetic sensor array including a plurality of magnetic sensors mounted to a flexible platform.

In yet another embodiment, a non-transitory computer-readable storage medium for locating an implanted device including magnetic coils within a subject is provided. The non-transitory computer-readable storage medium includes instructions that, when executed by a processor, cause the processor to calibrate a magnetic sensor array to create a database of sensor responses corresponding to various implant locations and orientations, instruct the implanted device to power the magnetic coils, receive a measured magnetic field acquired by the magnetic sensor array, and calculate a position of the implanted device based on the measured magnetic field.

In one embodiment, the instructions further cause the processor to output the calculated position.

In one embodiment, to calibrate the magnetic sensor array, the instructions cause the processor to calibrate the magnetic sensor array using a computer simulation.

In one embodiment, to calibrate the magnetic sensor array, the instructions cause the processor to calibrate the magnetic sensor array using measurements acquired from an actual implant.

In one embodiment, to calculate a position, the instructions cause the processor to calculate the position by comparing the measured magnetic field to the sensor responses in the database.

In one embodiment, to calibrate the magnetic sensor array, the instructions cause the processor to calibrate a magnetic sensor array including a plurality of magnetic sensors mounted to a rigid platform.

In one embodiment, to calibrate the magnetic sensor array, the instructions cause the processor to calibrate a magnetic sensor array including a plurality of magnetic sensors mounted to a flexible platform.

In yet another embodiment, a method for locating an implanted device including magnetic coils within a subject is provided. The method includes storing subject data associated with the subject in a memory, calibrating a magnetic sensor array to create a database of sensor responses corresponding to various implant locations and orientations, positioning the magnetic sensor array proximate the subject near an expected position of the implanted device, instructing the implanted device to power the magnetic coils, measuring, using the magnetic sensor array, a magnetic field generated by the implanted device, transmitting the measured magnetic field to a position detection module, calculating, using the position detection module, a position of the implanted device based on the measured magnetic field, and storing the calculated position as position data in the memory, the position data stored in associated with the subject data.

In one embodiment, the method further includes outputting the calculated position.

In one embodiment, calibrating the magnetic sensor array includes calibrating the magnetic sensor array using a computer simulation.

In one embodiment, calibrating the magnetic sensor array includes calibrating the magnetic sensor array using measurements acquired from an actual implant.

In one embodiment, calculating a position includes calculating the position by comparing the measured magnetic field to the sensor responses in the database.

In one embodiment, calibrating a magnetic sensor array includes calibrating a magnetic sensor array including a plurality of magnetic sensors mounted to a rigid platform.

In one embodiment, calibrating a magnetic sensor array includes calibrating a magnetic sensor array including a plurality of magnetic sensors mounted to a flexible platform.

In yet another embodiment, a method for use by a clinician in detecting migration of an implanted device including magnetic coils within a subject is provided. The method includes calibrating a magnetic sensor array to create a database of sensor responses corresponding to various implant locations and orientations, measuring, using the magnetic sensor array, a first magnetic field generated by the implanted device at a first time, calculating a first position of the implanted device based on the first measured magnetic field, measuring, using the magnetic sensor array, a second magnetic field generated by the implanted device at a second time, calculating a second position of the implanted device based on the second measured magnetic field, and calculating a distance between the first position and the second position.

In one embodiment, calibrating a magnetic sensor array includes calibrating a magnetic sensor array including a plurality of magnetic sensors mounted to a rigid platform.

In one embodiment, calibrating a magnetic sensor array includes calibrating a magnetic sensor array including a plurality of magnetic sensors mounted to a flexible platform.

In one embodiment, calibrating the magnetic sensor array includes calibrating the magnetic sensor array using a computer simulation.

In one embodiment, calibrating the magnetic sensor array includes calibrating the magnetic sensor array using measurements acquired from an actual implant.

BRIEF DESCRIPTION OF THE DRAWINGS

The novel features of the disclosure are set forth with particularity in the claims that follow. A better understanding of the features and advantages of the present disclosure invention will be obtained by reference to the following detailed description that sets forth illustrative embodiments, in which the principles of the invention are utilized, and the accompanying drawings of which:

DETAILED DESCRIPTION

Figure 1:
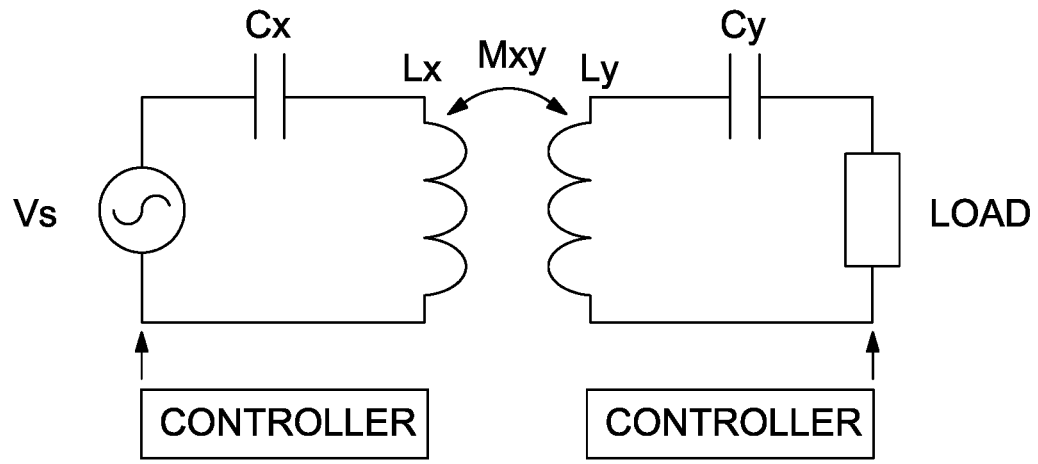
FIG. 1 illustrates a basic wireless power transfer system.

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

The systems and methods in certain embodiments include two systems associated with locating implanted wireless power transmission devices: i) a user interface for representing coupling between an external coil and an internal coil, and ii) a magnetic sensor for locating an implanted device. The user interface may be used, for example, by a patient, to facilitate aligning an external coil in real-time with an internal coil in order to improve the coupling between the external coil and the internal coil. The magnetic sensor, in contrast, assists a technician or professional in locating an implant within a subject. For example, the magnetic sensor may be used by an engineer to locate an implant within an animal, or may be used by a physician to locate an implant within a patient. This may be useful, for example, to help the clinician assess migration of the implant over time, ensure adequate coupling has been maintained, etc. In certain embodiments, the magnetic sensor is configured to allow the user to determine the gross location or region of the implant.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the disclosure will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In general, most of the flux from the transmitter coil does not reach the receiver coil. The amount of flux generated by the transmitter coil that reaches the receiver coil is described by "k" and is referred to as the "coupling coefficient." In general, the alignment is adequate if the resulting coupling coefficient k exceeds some minimum threshold $k_{min}$. It is preferable if the alignment results in a coupling coefficient close to an optimum value $k_{opt}$. The optimum value $k_{opt}$ is always larger than the minimum value $k_{min}$, and smaller than or equal to a maximum coupling coefficient value $k_{max}$. In some embodiments, $k_{min}$ is about 0.01, and $k_{max}$ is about 0.2.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy=k\sqrt{Lx \cdot Ly}$$

In the exemplary system a power source Vs can be in series with a transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (as shown in FIG. 1) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency, f, is 250 kHz. Then, for each cycle the load removes a certain amount of energy from the resonance:

$$e_L = \frac{P_L}{f} = 60 \; \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2} L i^2$$

$$i_y = \sqrt{\frac{2e_y}{L}} = 3.74 \; \text{A peak}$$

$$v_y = \omega L_y i_y = 352 \; \text{V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given k of 0.05:

$$e_x = \frac{420 \; \mu J}{0.05} = 8.4 \; mJ$$

For the same circuit the self inductance of the transmitter coil was 146 uH as mentioned above. This results in:

$$i_x = \sqrt{\frac{2e_x}{L}} = 10.7 \; \text{A peak}$$

$$v_x = \omega L_x i_x = 2460 \; \text{V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and all other conditions being equal, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
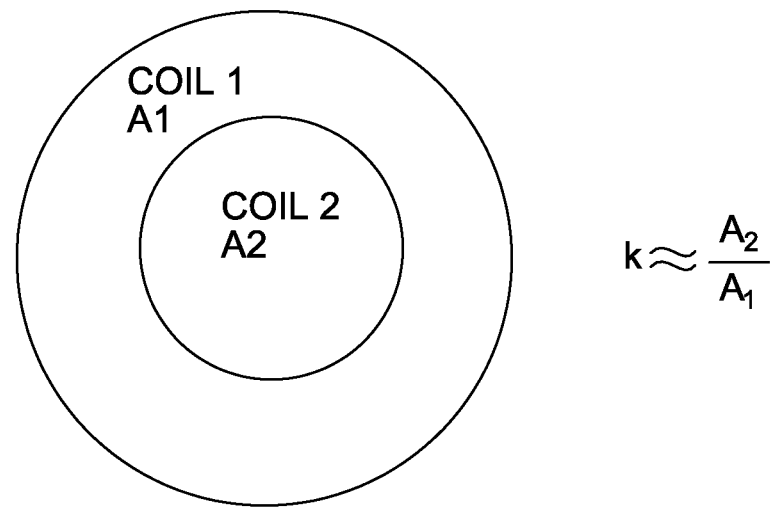
FIG. 2 illustrates magnetic coupling between a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
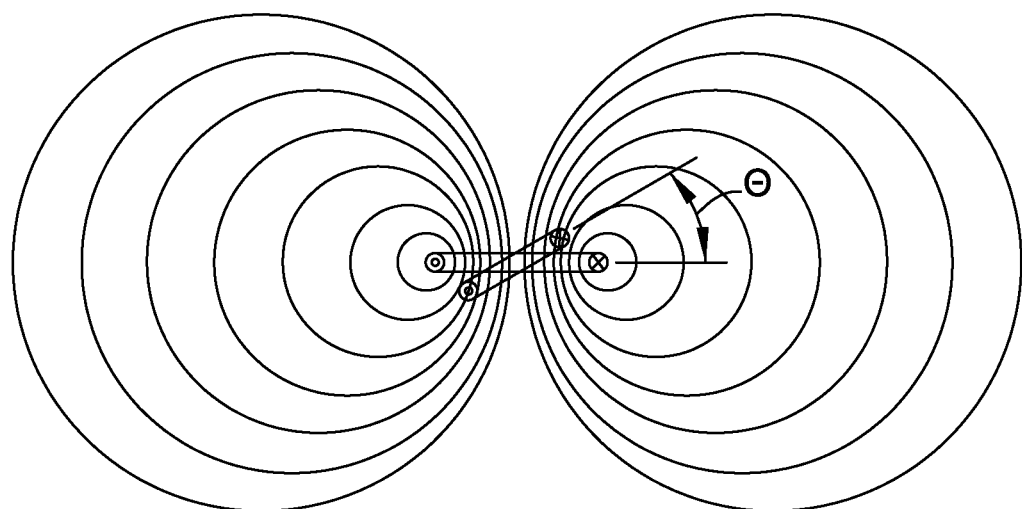
FIGS. 3A and 3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
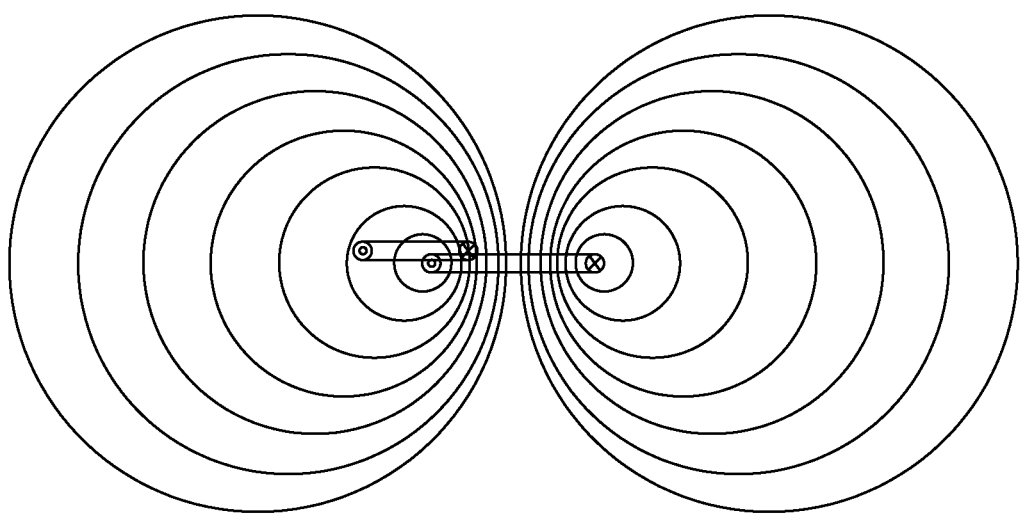

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy} = M_{yx}$$

As described above, a typical TET system can be subdivided into two parts, the transmitter and the receiver. Control and tuning may or may not operate on the two parts independently. For example, as shown in FIG. 1, the transmitter or the receiver or both may include a controller. The goal of this invention is to minimize the effect of relative spatial position and orientation on the magnetic field power transfer rate between a transmitter and a receiver.

User Interface for Determining Coupling

The user interface described herein may be used, for example, by a patient, to facilitate aligning an external coil with an internal coil in order to improve the coupling between the external coil and the internal coil. In some cases, the patient may desire to adjust the position of the external coil for comfort or other reasons and uses the user interface to ensure adequate coupling has been maintained. The exemplary user interface is designed to be intuitive for an untrained individual, and to improve precision and speed of alignment when used by an untrained individual.

Figure 4:
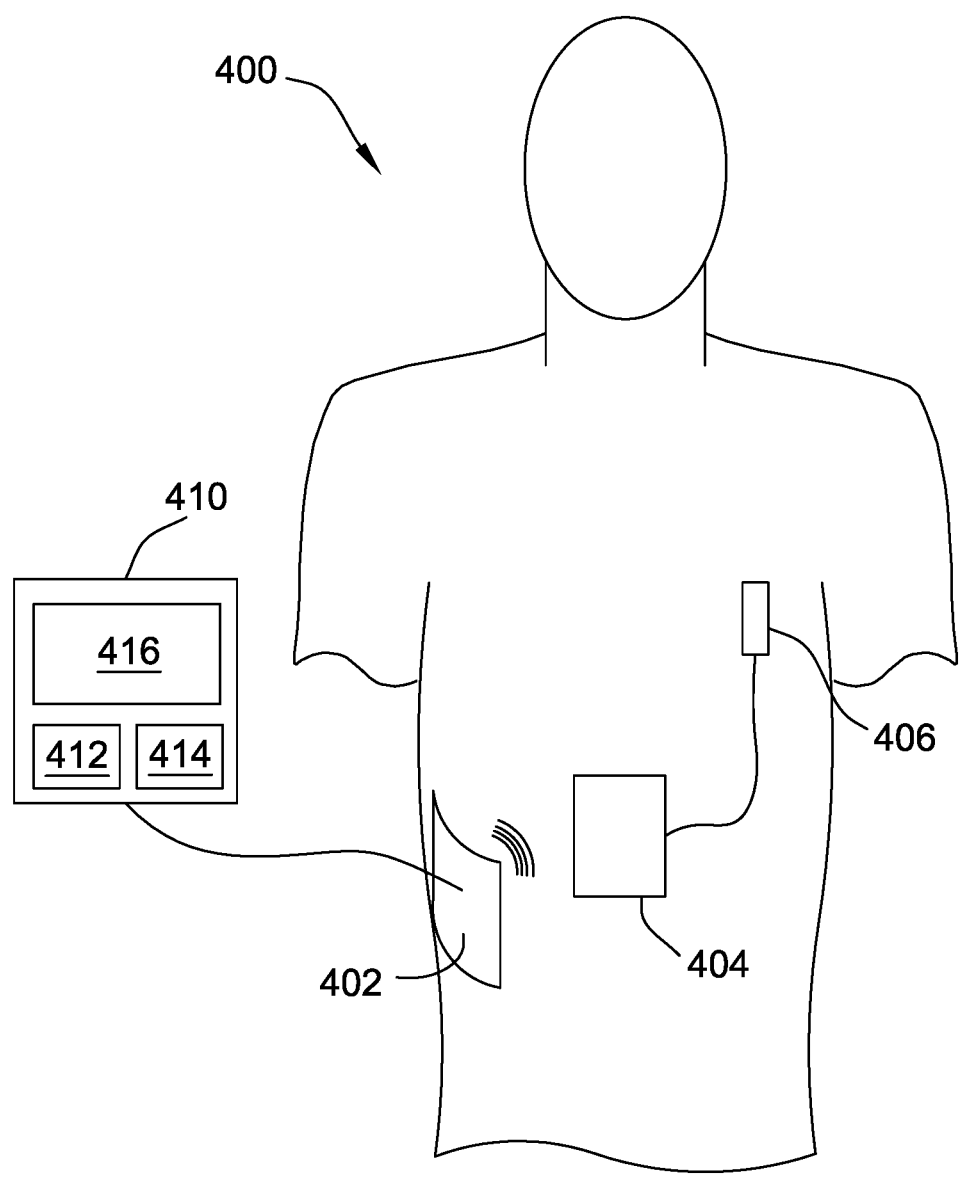
FIG. 4 illustrates a patient placing an external coil.

FIG. 4 illustrates a patient 400 placing an external coil 402. In the illustrated embodiment, the external coil 402 is operating in a test mode for coupling the external coil 402 to an implanted coil 404. The implanted coil 404 is a receiver for wirelessly receiving power from the external coil 402 (a transmitter), for powering an implanted device 406. For example, the implanted device 406 may include a pacemaker or heart pump.

The external coil 402 is communicatively coupled to a computing device 410, for example, via wired or wireless connection, such that external coil 402 may receive signals from and transmit signals to the computing device 410. In some embodiments, the computing device 410 is a power source for the external coil 402. In other embodiments, the external coil 402 is coupled to an alternative power supply (not shown). The computing device 410 includes a processor 412 in communication with a memory 414. In some embodiments, executable instructions are stored in the memory 414. In the illustrated embodiment, the computing device 410 performs one or more operations described herein by programming the processor 412. For example, the processor 412 may be programmed by encoding an operation as one or more executable instructions and by providing the executable instructions in the memory 414.

The processor 412 may include one or more processing units (e.g., in a multi-core configuration). Further, the processor 412 may be implemented using one or more heterogeneous processor systems in which a main processor is present with secondary processors on a single chip. In another illustrative example, the processor 412 may be a symmetric multi-processor system containing multiple processors of the same type. Further, the processor 412 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein.

In the illustrated embodiment, the memory 414 is one or more devices that enable information such as executable instructions and/or other data to be stored and retrieved. The memory 414 may include one or more computer readable media, such as, without limitation, dynamic random access memory (DRAM), read-only memory (ROM), electrically erasable programmable read-only memory (EEPROM), static random access memory (SRAM), a solid state disk, and/or a hard disk. The memory 414 may be configured to store, without limitation, application source code, application object code, source code portions of interest, object code portions of interest, configuration data, execution events and/or any other type of data.

The computing device 410 further includes a user interface (UI) 416. The UI 416 presents information to a user (e.g., patient 400). For example, the UI 416 may include a display adapter (not shown) that may be coupled to a display device, such as a cathode ray tube (CRT), a liquid crystal display (LCD), an organic LED (OLED) display, and/or an "electronic ink" display. In some embodiments, the UI 416 includes one or more display devices. Further, in some embodiments, presentation interface may not generate visual content, but may be limited to generating audible and/or computer-generated spoken-word content. In the example embodiment, the UI 416 displays one or more representations designed to aid the patient 400 in placing the external coil 402 such that the coupling between the external coil 402 and the implanted coil 404 is optimal. Accordingly, the patient 400 monitors the UI 416 while maneuvering the external coil 402 about their body to determine whether they are accurately and precisely positioning the external coil 402.

Figure 5:
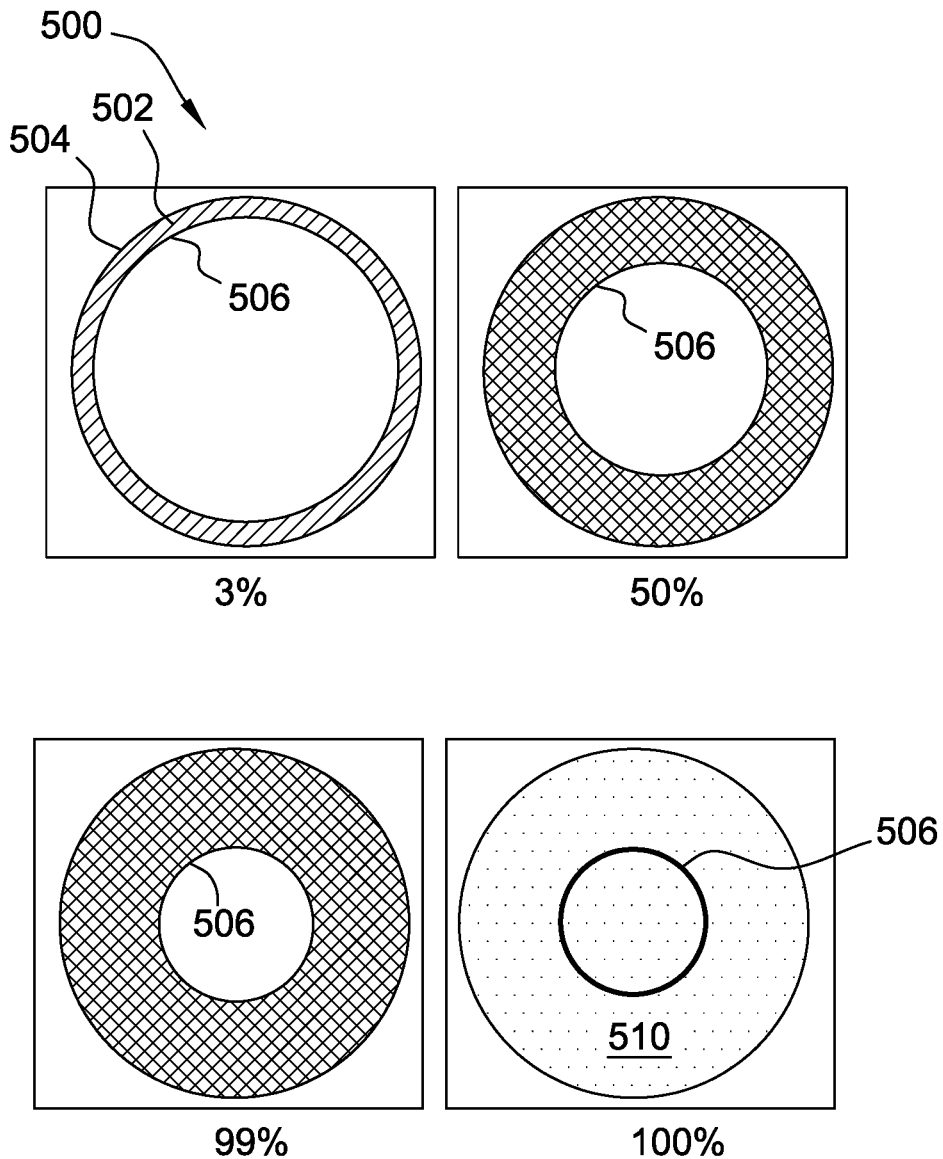
FIG. 5 illustrates of an icon for display on a user interface (UI) to communicate to the patient details about coupling between the external coil and an implanted coil.

FIG. 5 illustrates one embodiment of an icon 500 for display on the UI 416 to communicate to the patient 400 details about the coupling (i.e., coupling coefficient k) between the external coil 402 and the implanted coil 404 (all shown in FIG. 4). In particular, the progression of the icon 500 illustrated in FIG. 5 shows how the icon 500 communicates a progressive increase in the coupling to the patient 400. In the illustrated embodiment, the icon 500 is represented as a circle 502. In one or more alternative embodiment, the icon 500 may be represented as a ring, a square, a filleted square, and/or any other shape. In preferred embodiments, the icon 500 is represented as a shape with two-fold symmetry. In the illustrated embodiment, the circular icon 500 has a fixed outer diameter 504 and a variable inner diameter 506. As the coupling increases, the inner diameter 506 shrinks, such that the icon 500 gives the patient 400 a sense of approaching a "bull's eye" as the coupling increases. In this way, the icon 500 makes it apparent to the patient 400 that they are "on the right track" in positioning the external coil 402. In addition, in the illustrated embodiment, the inner diameter 506 shrinks continuously as the coupling increases. In this way, the icon 500 aids the patient 400 in achieving optimum accuracy in the positioning of the external coil 402. In an alternative embodiment, the inner diameter 506 shrinks in discrete increments. As shown in FIG. 5, in this embodiment, icon 500 also includes a textual indication (e.g., a displayed percentage) indicating the level of coupling.

When a near optimum coupling is achieved (e.g., when the external coil 402 is within about 1 cm to about 2 cm of the position of the implanted coil 404), the inner diameter 506 "jumps" from its current size at the time of optimum coupling down to zero. In other words, when the near optimum coupling is achieved, the entire icon 500 is suddenly lit up. This is illustrated in FIG. 5 by the substantially filled icon 510 designated by "100%." In this way, the icon 500 gives the patient 400 substantially immediate feedback that the positioning of the external coil 402 is near optimum and gives the patient 400 confidence that the external coil 402 is sufficiently coupled to the implanted coil 404.

In some embodiments, the icon 500 is color-coded to provide additional information to the patient 400 regarding the status of the positioning of the external coil 402. This is illustrated in FIG. 5 with the single hatching of the icon 500 at "3%" of an optimal coupling, the single hatching representing, for example, a red color; the cross-hatching of the icon 500 at "50%" and "99%" representing, for example, a yellow color; and the dotted hatching of the filled icon 510 at "100%" representing, for example, a green color. In at least one alternative embodiment, the icon 500 may not be color-coded.

In addition to or as an alternative to the color-coding, to avoid confusion for a patient 400 with reduced color vision (e.g., a colorblind patient), an intensity of the icon 500 (e.g., an amount of light emitted thereby) is varied to represent the status of the positioning of the external coil 402. For example, the intensity of the icon 500 may increase as the coupling increases. In another embodiment, the intensity of the icon 500 is maintained substantially constant. Moreover, in some embodiments, the user interface 416 may further include audio capability, such that the status of the coupling is represented using ascending tones (e.g., to represent increases in coupling) and/or descending tones (e.g., to represent decreases in coupling). The tones may additionally or alternatively pulse, and the frequency may indicate the status of the coupling. In one embodiment, a continuous tone (e.g., a continuous ascending tone) may represent an increase in the coupling, and a pulsing tone may indicate a decrease in the coupling. Additionally or alternatively, a sonic intensity may indicate the status of the coupling.

In some embodiments, the user interface 416 may further include a directional indicator (not shown), such as arrows, chevrons, dots, lines, curves, and/or other geometric shapes. The directional indicator may light up or activate to indicate to the patient 400 which direction to move the external coil 402 to increase the coupling with the implanted coil 404.

Figure 6:
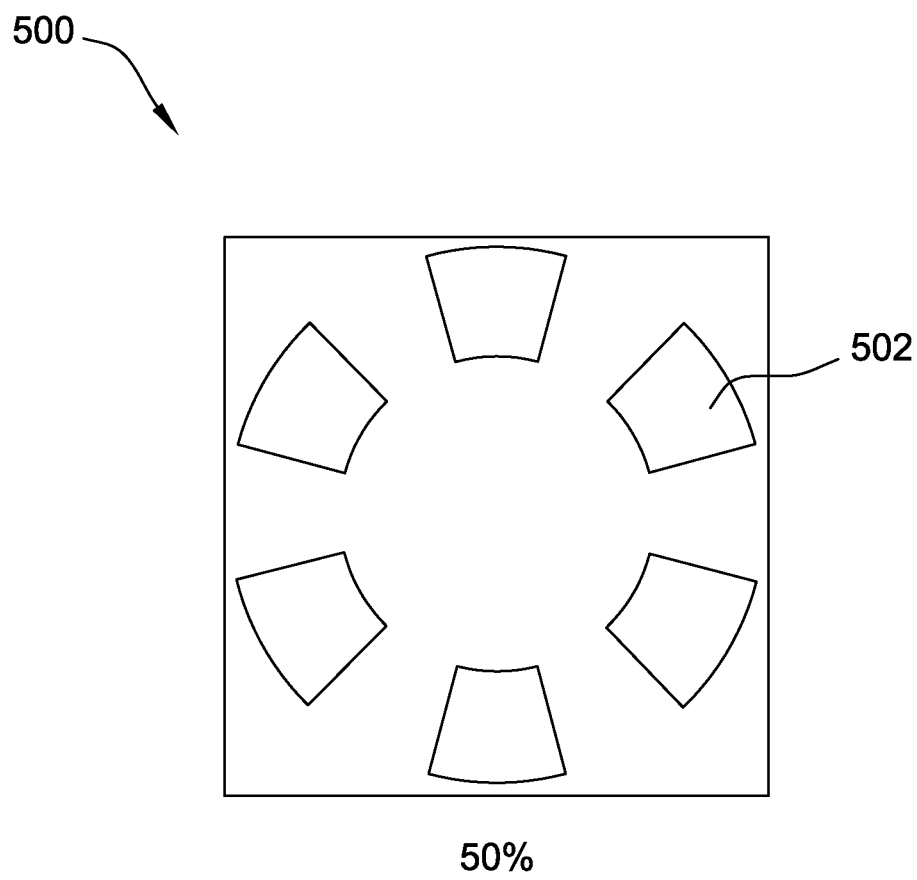
FIG. 6 illustrates the icon shown in FIG. 5 when the coupling is decreasing.

When the coupling is increasing, as shown in FIG. 5, the icon 500 includes a continuous circle 502. However, as shown in FIG. 6, in this embodiment, when the coupling is decreasing, the circle 502 becomes broken. Accordingly, the icon 500 quickly indicates to the patient 400 whether the coupling is currently increasing or decreasing, regardless of the immediate value of the coupling.

Figure 7:
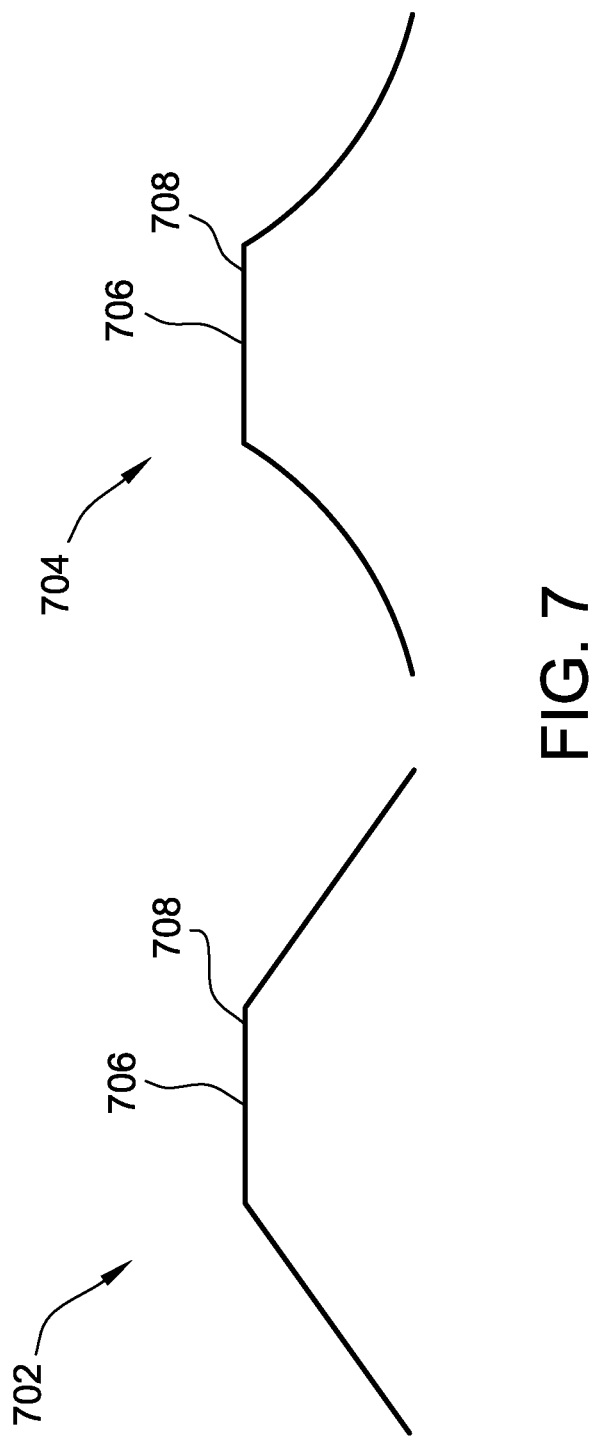
FIG. 7 illustrates a first sigmoid curve and a second sigmoid curve that may control the rate at which the icon shown in FIGS. 5 and 6 changes.

In this embodiment, as the coupling increases towards the optimum coupling or decreases away from the optimum coupling, the rate at which icon 500 changes is based on a sigmoid curve. For example, FIG. 7 illustrates a first sigmoid curve 702 and a second sigmoid curve 704 that may control the rate at which the icon 500 changes. A center 706 of the first and second sigmoid curves 702 and 704 corresponds to the optimum coupling. Both sigmoid curves 702 and 704 include a planar segment 708 surrounding the center 706 that creates a forgiving "sweet spot". When the coupling falls within the planar segment 708, the filled icon 510 (shown in FIG. 5) is displayed. The first sigmoid curve 702 is a linear sigmoid curve, and the second sigmoid curve 704 is a relatively weak convex sigmoid curve. These curves 702 and 704 provide for a good trade-off between registering a signal when the coils 402 and 404 are grossly misaligned and the final alignment accuracy. Alternatively, any suitable curve may be used to control the rate at which the icon 500 changes. For example, in some embodiments, planar segment 708 is not included in the sigmoid curve.

The update/refresh rate of the UI 416 can vary. That is, the update/refresh rate can be chosen based on typical coil movement speed during alignment, desired alignment accuracy, and the chosen icon/sigmoid combination. For example, the speed at which the patient 400 moves the coil may be approximately 1 meter per second (m/s). Accordingly, if accuracy of ±1 cm is desired, and if the planar segment 708 of the sigmoid curve has a length corresponding to approximately ⅛ of the diameter of the "detection zone" (i.e., the area where the icon 500 registers any coupling), the refresh rate may for the UI 416 may be a few times larger than 1 (m/s)/8 (cm)=12.5 Hz to avoid the possibility of traversing the detection zone without the UI responding. If the refresh rate is just barely bigger than 12.5 Hz, detection would likely be guaranteed if the chord was along a detection zone diameter, but not any off-center chords. In contrast if the refresh rate is 3-4 times larger than 12.5 Hz, detection would likely be guaranteed in most situations.

Using the UI 416 described herein, facilitates reducing the time it takes the patient 400 to align the external coil 402 with the implanted coil 404, improving patient quality of life and reducing worries and concerns about misalignment.

Magnetic Sensor for Locating an Implanted Device

The magnetic sensor described herein assists a trained individual in locating an implant within a subject. For example, the magnetic sensor may be used by an engineer to locate an implant within an animal, or may be used by a physician to locate an implant within a patient. The information gained from using the magnetic sensor may be used for analysis, not necessarily immediate action. For example, a physician may use the magnetic sensor to detect migration of an implant over time for clinical decision-making, such as, to determine whether the implant is exerting pressure on a particular organ or if sutures holding the implant in place have failed. This may be helpful because typically no external coil is present when the trained individual (e.g., clinician) uses the magnetic sensor. Additionally, the patient's physiology often changes over time which can affect the location of the implanted coil relative to the external coil. For example, the patient may lose or gain weight, in particularly fatty tissue between the implant and skin line. The information from the sensor can be used by the physician to make adjustments or other clinical decisions.

Figure 8:
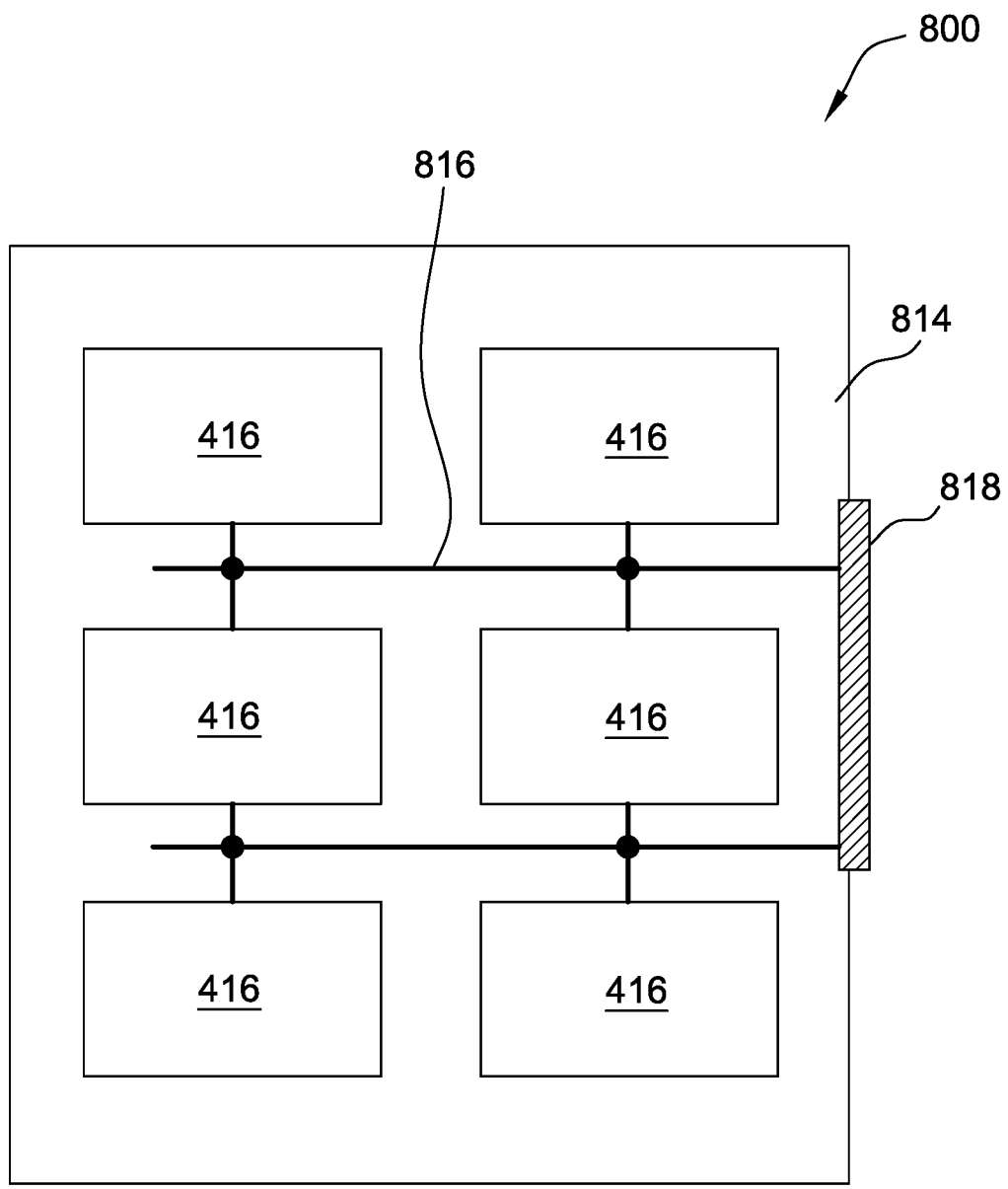
FIG. 8 illustrates a magnetic sensor array with multiple magnetic sensors.

FIG. 8 shows one embodiment of a magnetic sensor array 800 that may be used to locate an implanted device that includes magnetic coils, such as, for example, implanted coil 404 (shown in FIG. 4). In various embodiments, the magnetic sensor array 800 includes six magnetic sensors 802, 804, 806, 808, 810, 812. The magnetic sensors 802, 804, 806, 808, 810, 812 may include, for example, pick-up coils, Hall probes, MEMS-based magnetic field sensors, and/or any type of magnetic sensor. In one embodiment, the magnetic sensors 802, 804, 806, 808, 810, 812 are mounted to a rigid platform 814. The rigid platform 814 may include, for example, plastic or another polymer. In another embodiment, the magnetic sensors 802, 804, 806, 808, 810, 812 are mounted to a flexible platform 814. In some embodiments, the flexible platform 814 can include KAPTON® or other polyimide films, polyester films, or cloth, such as cotton cloth. In these embodiments, the magnetic sensor array 800 may be incorporated into a garment (e.g., a belt or shirt) as long as the garment is stretched taut, such that the locations of the magnetic sensors 802, 804, 806, 808, 810, 812 are substantially well-defined.

When the magnetic sensors 802, 804, 806, 808, 810, 812 are free to move with respect to one another (e.g., when they are placed on a garment), it is possible (in the absence of other magnetic materials) to use the magnetic sensors 802, 804, 806, 808, 810, 812 to determine the location of each other if the magnetic sensors 802, 804, 806, 808, 810, 812 are pick-up coils or if each magnetic sensor 802, 804, 806, 808, 810, 812 is a Hall sensor with a small coil is placed around it. Specifically, energizing each coil and measuring the responses in the other coils creates a data set that uniquely defines locations of all coils (e.g., relative to a one of the coils that is used as a reference coil). Between any two circular coils, there are four degrees of freedom. Accordingly, for a system of six coils, a system of equations for all locations and angles between the magnetic sensors 802, 804, 806, 808, 810, 812 is uniquely defined and solvable using, for example, the Biot-Savart calculations and/or finite element analysis techniques.

In one embodiment, the magnetic sensors 802, 804, 806, 808, 810, 812 are mounted to the platform 814 and can be interconnected using a flexible circuit or discrete cabling 816 to allow communications between the magnetic sensors 802, 804, 806, 808, 810, 812. The magnetic sensor array 800 can also include a connector 818 to, for example, an external power supply and/or an external computing device.

As shown in FIG. 8, the magnetic sensors 802, 804, 806, 808, 810, 812 are each connected to every other magnetic sensor 802, 804, 806, 808, 810, 812 with cabling 816, but it should be understood that the specific connection patterns can vary (e.g., in some embodiments the magnetic sensors 802, 804, 806, 808, 810, 812 may be coupled in series). Moreover, although the magnetic sensors 802, 804, 806, 808, 810, 812 are shown in a 2D array in this embodiment, with each of the magnetic sensors 802, 804, 806, 808, 810, 812 having the same orientation, it should be understood that various other configurations may be implemented. For example, the magnetic sensors 802, 804, 806, 808, 810, 812 may be arranged in a one-dimensional (1D) array (e.g., in series) or a 3D array. Moreover, the magnetic sensors 802, 804, 806, 808, 810, 812 may be arranged such that one or more of the magnetic sensors 802, 804, 806, 808, 810, 812 are in one or more different planes and/or have one or more different orientations from the others of magnetic sensors 802, 804, 806, 808, 810, 812. In addition, it should be understood that the magnetic sensor array 800 may include more than six magnetic sensors.

In this embodiment, the pick-up coils for each magnetic sensors 802, 804, 806, 808, 810, 812 are be approximately 5 mm in diameter. Alternatively, the pick-up coils may have any suitable size. For example, the pick-up coils may be as small as 1 mm in diameter. The active element in each magnetic sensors 802, 804, 806, 808, 810, 812 may be even smaller (e.g., dimensions on the order of fractions of a millimeter), but may include packaging on the millimeter scale to facilitate handling of the sensor. Ultimately, sensor size is determined by application. For example, if the goal is centimeter-scale precision, magnetic sensors 802, 804, 806, 808, 810, 812 can't be much larger than a centimeter. However, larger sensors may be used if the number of sensors is increased (e.g., analyzing signal differences between overlapping sensors). Accordingly, magnetic sensors 802, 804, 806, 808, 810, 812 may have any size that enables them to function as described herein. To improve precision in locating the implanted device, magnetic sensors 802, 804, 806, 808, 810, 812 may be spread evenly over an imagined sphere surrounding the implant. In contrast, if magnetic sensors 802, 804, 806, 808, 810, 812 clustered together into a space that is small compared to a distance between magnetic sensors 802, 804, 806, 808, 810, 812 and the implanted device, precision will generally be poorer.

To locate the implanted device, the magnetic sensor array 800 measures a magnetic field generated by the implanted device. Based on the measured magnetic field, a computing device (also referred to as a position detection module) communicatively coupled to the magnetic sensor array 800 calculates the precise position of the implanted device relative to the magnetic sensor array 800. Further, the calculated position may be displayed on a display device and/or transmitted to another device. The calculated position may also be stored in a memory as position data. For example, the position data may be stored in association with subject data that is associated with the subject. The computing device may be external to the magnetic sensor array 800 or may be a microprocessor integrated within the magnetic sensor array 800.

Figure 9:
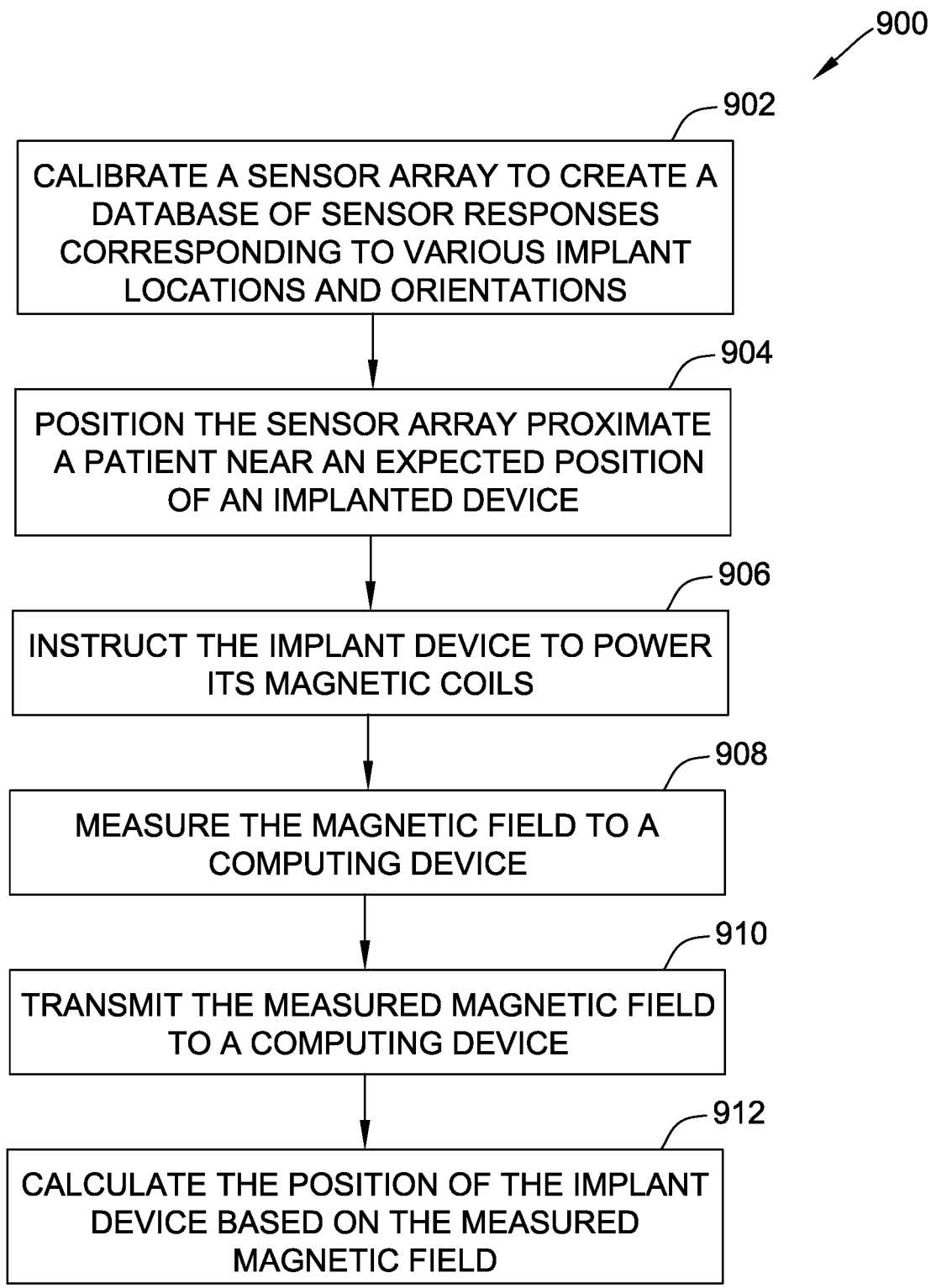
FIG. 9 illustrates a method for locating an implanted device.

FIG. 9 illustrates a flow chart of one embodiment of a method 900 for locating an implanted device. The method 900 may be performed, for example, using the magnetic sensor array 800 (shown in FIG. 8). The method 900 includes calibrating 902 the sensor array to create a database of sensor responses corresponding to various implant locations and orientations. The sensor responses may be stored, for example, in a memory. The calibration 902 may be based on a computer simulation or upon measurements taken relative to an actual implanted device.

The calibrated sensor array is then positioned 904 proximate the subject (e.g., an animal or patient) near an expected location of the implanted device. Then, the implanted device is instructed 906 to power its magnetic coils for a predetermined period of time (e.g., a fraction of a second). While the magnetic coils are powered, the calibrated sensor array measures 908 the magnetic field generated by the implanted device. The measured magnetic field is transmitted 910 to a computing device, and the computing device calculates 912 the position of the implanted device based on the measured magnetic field. Specifically, in this embodiment, the computing device calculates 912 the position of the implanted device by comparing the measured magnetic field with the sensor responses generated calibration 902 of the sensor array. The comparison may be made using a variety of data matching methods (e.g., least square fit) and interpolation techniques may be used to improve accuracy and/or reduce the size of the database.

Notably, magnetic sensor array 800 may be used to detect migration of the implanted device over time. For example, a position tracking module (i.e., a computing device) may track the position of the implanted device. The position tracking module may store an initial position detected at a first time, and at least one subsequent position detected at a later time. By calculating the distance (if any) between the initial position and the at least one subsequent position, the position tracking module is able to determine how far the implanted device has migrated.

Accordingly, using the systems and methods described herein, a magnetic sensor array may be used to locate an implant having magnetic coils quickly and easily. The magnetic sensor array provides immediate feedback about the precise location of the implant, and does not require uncommon or rare equipment to operate.

Notably, this disclosure can pertain to any device that receives power wirelessly at a distance from the power source, including all types of electronics (cell phones, portable computers, PDAs, mobile games, remote controls, etc.), electric cars, trains, and other vehicles, or any other device that uses electric power. The disclosure could be used to charge the batteries of any such device, or to power it directly. The disclosure does not rely on either the transmitter or receiver being in resonance, although it can take advantage of such systems.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents.

What is claimed is:

1. A system for locating an implanted device including magnetic coils within a subject, the system comprising:
    a magnetic sensor array comprising a plurality of magnetic sensors, the magnetic sensor array configured to measure a magnetic field generated by the implanted device; and a position detection module communicatively coupled to the magnetic sensor array, the position detection module configured to:
  calibrate the magnetic sensor array to create a database of sensor responses corresponding to various implant locations and orientations;
  receive the measured magnetic field from the magnetic sensor array; and
  calculate a position of the implanted device based on the measured magnetic field.

2. The system of claim 1, wherein the magnetic sensor array comprises six magnetic sensors.

3. The system of claim 1, further comprising a display device configured to display the calculated position to a user.

4. The system of claim 1, wherein the magnetic sensor array is configured to be calibrated using measurements acquired from an actual implant.

5. The system of claim 1, wherein the plurality of magnetic sensors are mounted to a rigid platform.

6. The system of claim 1, wherein the plurality of magnetic sensors are mounted to a flexible platform.

7. The system of claim 1, wherein the position detection module is further configured to transmit the calculated position to another device.

8. The system of claim 1, further comprising a position tracking module communicatively coupled to the magnetic sensor array and configured to:
  store an initial position of the implanted device;
  store a subsequent position of the implanted device; and
  calculate a distance between the initial position and the subsequent position.

9. A method for locating an implanted device including magnetic coils within a subject, the method comprising:
  calibrating a magnetic sensor array to create a database of sensor responses corresponding to various implant locations and orientations;
  positioning the magnetic sensor array proximate the subject near an expected position of the implanted device;
  instructing the implanted device to power the magnetic coils;
  measuring, using the magnetic sensor array, a magnetic field generated by the implanted device;
  transmitting the measured magnetic field to a position detection module; and
  calculating, using the position detection module, a position of the implanted device based on the measured magnetic field.

10. The method of claim 9, further comprising outputting the calculated position.

11. The method of claim 9, wherein the calibrating of the magnetic sensor array further comprises calibrating the magnetic sensor array using a computer simulation.

12. The method of claim 9, wherein the calibrating of the magnetic sensor array further comprises calibrating the magnetic sensor array using measurements acquired from an actual implant.

13. The method of claim 9, wherein the calculating of the flail position further comprises calculating the position by comparing the measured magnetic field to the sensor responses in the database.

14. The method of claim 9, wherein the calibrating of the magnetic sensor array further comprises calibrating a magnetic sensor array including a plurality of magnetic sensors mounted to a rigid platform.

15. The method of claim 9, wherein the calibrating of the magnetic sensor array further comprises calibrating a magnetic sensor array including a plurality of magnetic sensors mounted to a flexible platform.

* * * * *